(12) United States Patent
Ding et al.

(10) Patent No.: US 8,147,802 B2
(45) Date of Patent: Apr. 3, 2012

(54) CHELATOR-FUNCTIONALIZED NANOPARTICLES

(75) Inventors: Zhebo Ding, Niskayuna, NY (US); Brian James Grimmond, Clifton Park, NY (US); Michael Luttrell, Clifton Park, NY (US); Slawomir Rubinsztajn, Ballston Spa, NY (US); David Cheney deMoulpied, New Baltimore, NY (US); Margaret L. Blohm, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 1191 days.

(21) Appl. No.: 11/864,453

(22) Filed: Sep. 28, 2007

(65) Prior Publication Data

US 2009/0087381 A1 Apr. 2, 2009

(51) Int. Cl.
*A61K 49/06* (2006.01)
*A61K 49/18* (2006.01)

(52) U.S. Cl. ............... 424/9.3; 424/9.1; 424/489
(58) Field of Classification Search ............ 424/1.11, 424/9.36, 9.6, 489, 490
See application file for complete search history.

(56) References Cited

U.S. PATENT DOCUMENTS

2006/0165591 A1* 7/2006 Gries et al. ............ 424/1.11
2008/0286370 A1* 11/2008 Kuebelbeck et al. ...... 424/490

* cited by examiner

*Primary Examiner* — Michael G Hartley
*Assistant Examiner* — Jagadishwar Samala
(74) *Attorney, Agent, or Firm* — Paul J. DiConza (57) ABSTRACT

Provided herein are chelator-functionalized nanoparticles comprising a passive core; and an active coating that demonstrate T1 magnetic resonance pattern upon exposure to a magnetic field. Also provided are methods of making such chelator-functionalized nanoparticles as well as imaging methods using the nanoparticles.

10 Claims, 9 Drawing Sheets

| Agent | Relaxivity $r_1$ | [Gd] | [Agent] |
|---|---|---|---|
| DI H$_2$O | - | - | - |
| Gd-DTPA Magnevist™ | 4.3/mM.s | 0.25 mM | 250 μM |
| Gd-DOTA-SiO$_2$ | 8.1/mM.s | 0.25 mM | 168 nM |
| Gd-EDTA-SiO$_2$ | 16.6/mM.s | 0.25 mM | 50 nM |

FIG. 9

CHELATOR-FUNCTIONALIZED NANOPARTICLES

BACKGROUND

The invention relates generally to the field of magnetic resonance (MR) imaging using paramagnetic nanoparticles. In particular, the present invention is directed to chelator-functionalized nanoparticles, which may be used as T1 MR agents. Also provided herein are methods of making and methods of using chelator-functionalized nanoparticles.

Conventional clinical MR imaging contrast agents are small molecule based extracellular fluid agents that are used to provide broad anatomical contrast. However they are not optimal for the molecular imaging of oncology and cardiovascular diseases because of their short blood residence time and low signal per molecule.

Nanoparticle-based probes have shown great potential for bioimaging, diagnostic, and therapeutic purposes. Various nanoparticle-based MR imaging contrast agents have been investigated, including liposomes, micelles, vesicles, polymers, and proteins labeled with paramagnetic metal ions.

Although the T1 imaging mode is the preferred method of radiologists, there is no T1 nanoparticle composition currently available clinically. Furthermore, many nanoparticles suffer from poor stability due to aggregation. Size variation resulting from particle aggregation adversely affects the pharmacokinetic properties of the nanoparticle agents including variable distribution and poor elimination kinetics.

BRIEF DESCRIPTION

The advantages and features of the invention disclosed herein will be made more apparent from the description, drawings, and claims that follow.

One aspect of the invention provides a nanoparticle composition comprising a MR-passive core and a coating comprising functionalized organosilane moieties and a plurality of macrocyclic chelators. In another aspect, the invention provides a nanoparticle composition comprising a MR-passive core and a coating comprising functionalized organosilane moieties and a plurality of linear chelators. In all embodiments, the passive core may be selected from silicon (e.g., silica), aluminum, titanium, germanium and their derivatives wherein each of the plurality of chelators (i.e., macrocyclic or linear) is attached to the passive core via an organosilane moiety.

In some embodiments, the organosilane moiety is selected from N-(trimethoxysilylpropyl)ethylene diamine triacetic acid trisodium salt, N-(trimethoxysilylpropyl)-O-polyethylene oxide urethane, 3-(trimethoxysilylpropyl)succinic anhydride, 3-(trihydroxysilyl)propylmethylphosphonate, sodium salt, 2-(4-chlorosulfonylphenyl)ethyltrimethoxysilane, 3-aminopropyltriethoxysilane, or combinations thereof.

In some embodiments, the nanoparticle contains a plurality of non-paramagnetic counterions, wherein each of the plurality of non-paramagnetic counterions is complexed with the macrocyclic chelator. In alternative embodiments, non-paramagnetic ions (e.g., sodium, triethylammonium, potassium, calcium, dimegulamine, or combinations thereof) are substituted with paramagnetic ions (e.g., Gd, Fe, Mn, or combinations thereof) to produce a T1 MR agent. In some embodiments, 100 to 3000 paramagnetic ions are complexed with chelators attached to the nanoparticle.

In some embodiments, the macrocyclic chelator may be selected from 1,4,7,10-tetraazacyclododecane-1,4,7,10-tetraacetic acid (DOTA); 1,4,7,10-tetraazacyclododecane-1,4,7,10-tetrakis(2-propionic acid) (DOTMA); 1,4,7,10-tetraazacyclododecane-1,4,7,10-tetrakis[3-(4-carboxyl)-butanoic acid]; 1,4,7,10-tetraazacyclododecane-1,4,7,10-tetrakis(acetic acid-methyl amide); 1,4,7,10-tetraazacyclododecane-1,4,7,10-tetrakis(methylene phosphonic acid); p-isothiocyanatobenzyl-1,4,7,10-tetraazacyclododecane-1,4,7,10-tetraacetic acid (p-SCN-Bz-DOTA); 1,4,8,11-tetraazacyclododecane-1,4,8,11-tetraacetic acid (TETA); 1,4,7-tricarboxymethyl-1,4,7,10-tetraazacoclododecane (DO3A); or combinations thereof. In some embodiments, employing macrocyclic chelators, the nanoparticles form complexes with the paramagnetic ions through at least 5 coordinate links.

In another aspect, the relaxivity ratio (r2/r1) of the nanoparticle is less than 5. In one embodiment the r2/r1 ratio of the nanoparticle is greater than 1 and less than 2.5.

In another aspect, the size of the core and shell combined, measured by hydrodynamic diameter ($D_H$), is less than 250 nm. In one specific embodiment, the $D_H$ of the core and coating is less than 35 nm.

In another aspect, the nanoparticle further comprises a pharmacokinetic modifier (e.g., PEG, dextran, alkyl chain, ethylene glycol, poly L,L-lactic acid (PLLA), poly-caprolactone (PCL), 3-(trihydroxysilyl)-propylmethylphosphonate (THPMP), poly(2-methyl-2-oxazolidinone), poly(2-ethyl-2-oxazolidinone), poly(vinylpyrrolidinone), poly(arylamides), phosphonates, or combinations thereof).

In yet another aspect, provided herein are methods of producing water-soluble functionalized nanoparticles. The methods comprise the steps of (a) contacting a MR-passive core having a coating comprising functionalized organosilane moieties, wherein the organosilane moieties comprises amine functionalized group; (b) activating a macrocyclic chelator; (c) combining the activated macrocyclic chelator of step (b) with the amine-functionalized group present on the core and then (d) solubilizing the product of step (c) in a polar protic solvent to produce water-soluble nanoparticle macrocyclic chelator compound.

In some embodiments, the methods further include one or more purification steps. The purification steps may comprise of a high molecular weight purification method such as dialysis or ultrafiltration.

An aspect of the invention also encompasses a magnetic resonance imaging contrast agent in a physiologically acceptable medium, in which the magnetic resonance imaging contrast agent comprises nanoparticle composition comprising a MR-passive core and a coating. The coating comprises functionalized organosilane moieties and a plurality of macrocyclic chelators, wherein each of the plurality of macrocyclic chelators is attached to the passive core via an organosilane moiety.

An aspect of the invention also encompasses a method for obtaining an MR image of a tissue or an organ of an animal or a human subject comprising: administering to the subject, an effective amount of a magnetic resonance imaging contrast agent in a physiologically acceptable medium, wherein the magnetic resonance imaging contrast agent comprises the nanoparticles of the invention.

FIGURES

These and other features, aspects, and advantages of the present invention will become better understood when the following detailed description is read with reference to the accompanying drawings in which like characters represent like parts throughout the drawings, wherein.

DESCRIPTION

The following detailed description is exemplary and not intended to limit the invention of the application and uses of the invention. Furthermore, there is no intention to be limited by any theory presented in the preceding background of the invention of the following detailed description of the drawings.

To more clearly and concisely describe and point out the subject matter of the claimed invention, the following definitions are provided for specific terms that are used in the following description and the claims appended hereto.

As used herein the term "nanoparticle" refers to a substantially spherical or irregularly shaped particle with an average hydrodynamic diameter of between 1 nm and 500 nm.

As used herein the term "MR-passive core" refers to the inner component of the disclosed nanoparticles that is comprised of inorganic material (e.g., silica) that does not demonstrate an appreciable relaxivity.

The active coating comprising an active magnetic resonance (MR) contrast agent material and being disposed the inorganic core such that in the aggregate the core and shell form nanoparticle that is operable for use as an imaging agent in MR imaging.

As used herein, the term "average size" refers to the outer diameter (assuming a substantially spherical core) of the nanoparticle. In some embodiment the average size refers to the hydrodynamic diameter ($D_H$) of the nanoparticle. In some embodiments, the core size is consistent in a sample, with a distribution of less than 25%. The average size of silica nanoparticles may range from 15 nm to 20 nm as determined by TEM.

As used herein, the term "hydrodynamic diameter" ($D_H$) refers to the diameter of substantially spherical particle that would have a diffusion coefficient equal to that of the nanoparticle as measured by dynamic light scattering (DLS). $D_H$ values may vary depending on the medium in which the agent being measured is dispersed. Accordingly, unless otherwise indicated, the $D_H$ values described herein were measured using DLS where the agent is dispersed in buffer.

As used herein, the term ligand refers to an atom, ion, molecule or a compound that generally donates one or more of its electrons through a coordinate bond to, or shares its electrons through a covalent bond with, one or more atoms or ions.

The term "longitudinal relaxation time" or "T1" is the time constant that describes the exponential loss of magnetization in a plane longitudinal to the direction of the applied magnetic field, following a RF pulse that rotates the aligned magnetization into the longitudinal plane.

As used herein the term "transverse relaxation time" or "T2" refers to the time constant that describes exponential loss of magnetization in a plane transverse to the direction of the applied magnetic field, following a RF pulse that rotates the aligned magnetization into the transverse plane.

As used herein, the longitudinal relaxation rate is the reciprocal of T1, the relaxation time, and the r1 relaxivity refers to the change in relaxation rate (1/T1) per millimole of agent added.

As used herein, the transverse relaxation rate is the reciprocal of T2 relaxation time and the r2 relaxivity refers to the change in relaxation rate (1/T2) per millimole of agent added. In specific embodiments, the R2 relaxivity for agents, at room temperature and under a 1.5 Tesla field, ranges from 0.5 mM$^{-1}$/s$^{-1}$ to 50 mM$^{-1}$/s$^{-1}$.

As used herein, the term "r2/r1" refers to the ratio of relaxivities. r2/r1 may be used to quantify the type of contrast produced by an MR contrast agent. r2/r1 may determine whether a material is useful as either a positive (T1 agent) or negative (T2 agent) agent. In general, materials with r2/r1 ratios between 1 and 5 may function as a positive contrast agent and materials with r2/r1 ratios greater than 5 may function as a T2 contrast agent.

As used herein the term "paramagnetic metal ion", "paramagnetic ion" or "metal ion" refers to a metal ion that is magnetized parallel or antiparallel to a magnetic field to an extent proportional to the field. Generally, these are metal ions that have unpaired electrons. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In some embodiments, the paramagnetic ion is the lanthanide atom Gd(III), due to its high magnetic moment ($\mu2=63BM2$), a symmetric electronic ground state (S8).

As used herein the term "pharmacokinetic modifier" refers to any agent or moiety that may be appended to the nanoparticles to affect (e.g., increase or decrease) the absorption, distribution, metabolism, or elimination of a nanoparticle. Non-limiting examples of pharmacokinetic modifiers include polyketal polymers such as PEG, dextran, alkyl chain, amino acids, ethylene glycol, poly L,L-lactic acid (PLLA), polycaprolactone (PCL), 3-(trihydroxysilyl)-propylmethylphosphonate (THPMP), linear and branched poly(2-methyl-2-oxazolidinone), poly(2-ethyl-2-oxazolidinone), poly(vinylpyrrolidinone), poly(arylamides), phosphonates and combinations thereof.

As used herein the terms "zeta potential," "surface potential," and "surface charge" and the abbreviation "ξ" refers to a measurement of the electrostatic potential near the surface of the particle. As the zeta potential is affected by the solvent and ionic strength of the solvent, all zeta potential values reported herein are measured using buffer as the solvent unless otherwise indicated.

EMBODIMENTS

Provided herein are nanoparticle compositions comprising a MR-passive core and an organosilane-derived coating comprising plurality of chelators. The particle size or hydrodynamic diameter ($D_H$) of the chelator-functionalized nanoparticles including a core and a shell are typically less than 250 nm. In some preferred embodiments, the particle size is less than 35 nm. The provided nanoparticles, upon loading with paramagnetic ions, are useful as T1 MR contrast agents. Also, provided herein are methods of making and MR techniques employing such nanoparticles.

The Passive Core

In some embodiment the passive core may contain an inorganic material. The inorganic material may include elements such as silicon, aluminum, titanium, germanium etc and their derivatives, for example, oxides, nitrides, carbides, sulfides, phosphides, selenides, tellurides, borides and combinations thereof. In some particular embodiments, the passive core comprises silica. The MR-passive core does not demonstrate relaxivity that is appreciably greater than water. In some embodiments, the r1 value of the passive core is 0.4 $mM^{-1}s^{-1}$ when measured in a 1.5 Tesla MR machine. Thus, the passive cores of the provided nanoparticles do not include an appreciable amount paramagnetic ions or molecules.

The Shell

The MR-passive core of the chelator-functionalized nanoparticles is covered by an MR-active coating comprising functionalized organosilane moieties. Representative functionalized organosilane moieties include N-(trimethoxysilylpropyl)ethylene diamine triacetic acid trisodium salt, N-(trimethoxysilylpropyl)-O-polyethylene oxide urethane, 3-(trimethoxysilyl)propylsuccinic anhydride, 3-(trihydroxysilyl)propylmethylphosphonate, sodium salt, 2-(4-chlorosulfonylphenyl)ethyltrimethoxysilane, 3-aminopropyltriethoxysilane, or combinations thereof.

The coating contains functionalized organosilane moieties and a plurality of chelators (e.g., linear or macrocyclic chelators). Each of the chelators is attached to the core via an organosilane moiety. The nature of the chelator attachment to the organosilane moieties depends upon the number of available functional groups present in the chelators. In all embodiments, the chelator is attached to the organosilane through at least one of the functional group present in the chelator. In some embodiments, the chelator is attached to the organosilane through only one of the functional group present in the chelator. In alternative embodiments, the chelator is attached to the organosilane moieties through five functional groups present in the chelator.

The chelators on the nanoparticle may complex with a plurality of non-paramagnetic counterions or the chelator may complex with a plurality of paramagnetic counterions. Where the chelators are complex with a plurality of non-paramagnetic counterions, the nanoparticles are useful as precursor compounds for MR agents. Where the chelators are complex with a plurality of paramagnetic ions, the nanoparticles are useful as MR-active agents.

The non-paramagnetic counterions may be selected from sodium, triethylammonium, potassium, calcium, dimeglumine and combinations thereof.

In some embodiments, the chelator forms complexes with the paramagnetic metal via five coordinate links. In other embodiments, the chelator contains six or more functional groups. In one embodiment, the chelator is attached to the organosilane moiety through only one functional group present in the chelator leaving the remaining functional groups available to form complexes with the paramagnetic metal. Increased points of attachment between the chelator and the paramagnetic ion generally increases the stability of the resultant MR agent towards transmetallation.

Conventional metal chelating groups may be used, e.g., linear, cyclic and branched polyamino-polycarboxylic acids and phosphorus oxyacid equivalents, and other sulphur, or nitrogen ligands. Non-limiting examples of macrocyclic chelators may be selected from 1,4,7,10-tetraazacyclododecane-1,4,7,10-tetraacetic acid (DOTA), 1,4,7,10-tetraazacyclododecane-1,4,7,10-tetrakis(2-propionic acid) (DOTMA), 1,4,7,10-tetraazacyclododecane-1,4,7,10-tetrakis[3-(4-carboxyl)-butanoic acid], 1,4,7,10-tetraazacyclododecane-1,4,7,10-tetrakis(acetic acid-methyl amide), 1,4,7,10-tetraazacyclododecane-1,4,7,10-tetrakis(methylene phosphonic acid), or p-isothiocyanatobenzyl-1,4,7,10-tetraazacyclododecane-1,4,7,10-tetraacetic acid (p-SCN-Bz-DOTA) or combinations thereof.

Suitable linear chelating molecules include, but are not limited to ethylenediaminetetraacetic acid (EDTA), diethylenetriaminepentaacetic acid (DTPA), Triethylenetetraminehexacetic acid (TTHA), N-tris(2-aminoethyl)amine-N',N',N'',N'',N''',N'''-hexaacetate (TTAHA), etc.

Molecules useful for chelating other ions (such as, for example, Fe(III), Mn(II), or Cu(II)) include bis(thiosemicarbazone) and derivatives, porphyrins and derivatives, 2,3-bis (2-thioacetamido)propionates and derivatives, N,N'-bis(mercaptoacetyl)-2,3-diaminopropanoate, and bis (aminoethanethiol) and derivatives.

In some embodiments, the functional group in the chelator is attached to the coating of the nanoparticle through a spacer. Spacer groups may include, but are not limited to, alkyl and aryl groups, substituted alkyl and aryl groups, heteroalkyl (e.g., oxo groups), and heteroaryl groups. In some embodiments, the linker may include p-aminobenzyl, substituted p-aminobenzyl, diphenyl and substituted diphenyl, alkyl furan such as benzylfuran, carboxy, and straight chain alkyl groups of 1 to 10 carbons in length. In some particular embodiments, the linker may comprise p-aminobenzyl, methyl, ethyl, propyl, butyl, pentyl, hexyl, acetic acid, propionic acid, aminobutyl, p-alkyl phenols, 4-alkylimidazole, carbonyls, OH, COOH, or glycols.

The loading of paramagnetic metals on each nanoparticle determines the sensitivity of the nanoparticle as MR contrast agent. The number of paramagnetic metal ions per nanoparticle depends upon the size of the nanoparticle and the extent of the particle coating with chelators. For nanoparticles of 20-nm to 35 nm in hydrodynamic diameter the loading of paramagnetic metal may vary from 1500 to 5000 ions/nanoparticle. In some embodiments, the loading of paramagnetic metal ion to each nanoparticle is in the range of 100 to 3000 ions/nanoparticle. The paramagnetic metal ion may be Gd. In one embodiment, DOTA functionalized nanoparticles are loaded with 1500 Gd ions/nanoparticle. In other embodiments, the loading is 11000 Gd ions/nanoparticle for EDTA functionalized nanoparticles.

In some embodiments, the organosilane moieties may be further functionalized with pharmacokinetic modifier. Non-limiting examples of the pharmacokinetic modifier include dextran, PEG, alkyl chain, ethylene glycol, poly (L) lactic acid, polycaprolactone, polyurethane, 3-(trihydroxysilyl)-propylmethylphosphonate (THPMP), amino acids, linear and branched poly(2-methyl-2-oxazolidinone), poly(2-ethyl-2-oxazolidinone), poly(vinylpyrrolidinone), poly(arylamides), phosphonates, phosphates, carboxylates, or combinations thereof. In one embodiment, THPMP is the pharmacokinetic modifier.

In some embodiments, the nanoparticle of the invention is negatively charged with zeta potential less than zero, less than −6 mv, less than −30 mV, or less than −70 mV.

The nanoparticles of the invention are preferably non-agglomerated with a polydispersity of less than 23% as determined by TEM.

The relaxivity values (r1) of control and chelator-functionalized nanoparticles were measured at pH 7 (10 mM $Et_3NHOAc$ buffer, 150 mM saline) using a 1.5 T MR relax meter and the values are shown in Table 1. The relaxivities of the chelated Gd species show an appreciable increase over the Gd chelate small molecule equivalent when bound to the silica nanoparticle, which is likely due to the reduced tumbling rate of the paramagnetic ion as reported previously for nonsocial and polymeric MR agents. The low r2/r1 values of 1.2 to 1.3 are consistent with those of agents suitable for use in T1 weighted MR imaging.

TABLE 1

| Agent | No. Gd · nanoparticle$^{-1}$ | R1 (mM$^{-1}$ · s$^{-1}$) | R2 (mM$^{-1}$ · s$^{-1}$) | R2/R1 | $D_H$ (nm) | ξ-potential (mV) |
|---|---|---|---|---|---|---|
| SiO$_2$GdDOTA | 1500 | 8.1 | 9.5 | 1.2 | 36 | −5 |
| SiO$_2$GdEDTA | 5000 | 16.2 | 21.5 | 1.4 | 25 | −7 |

Figure 9:
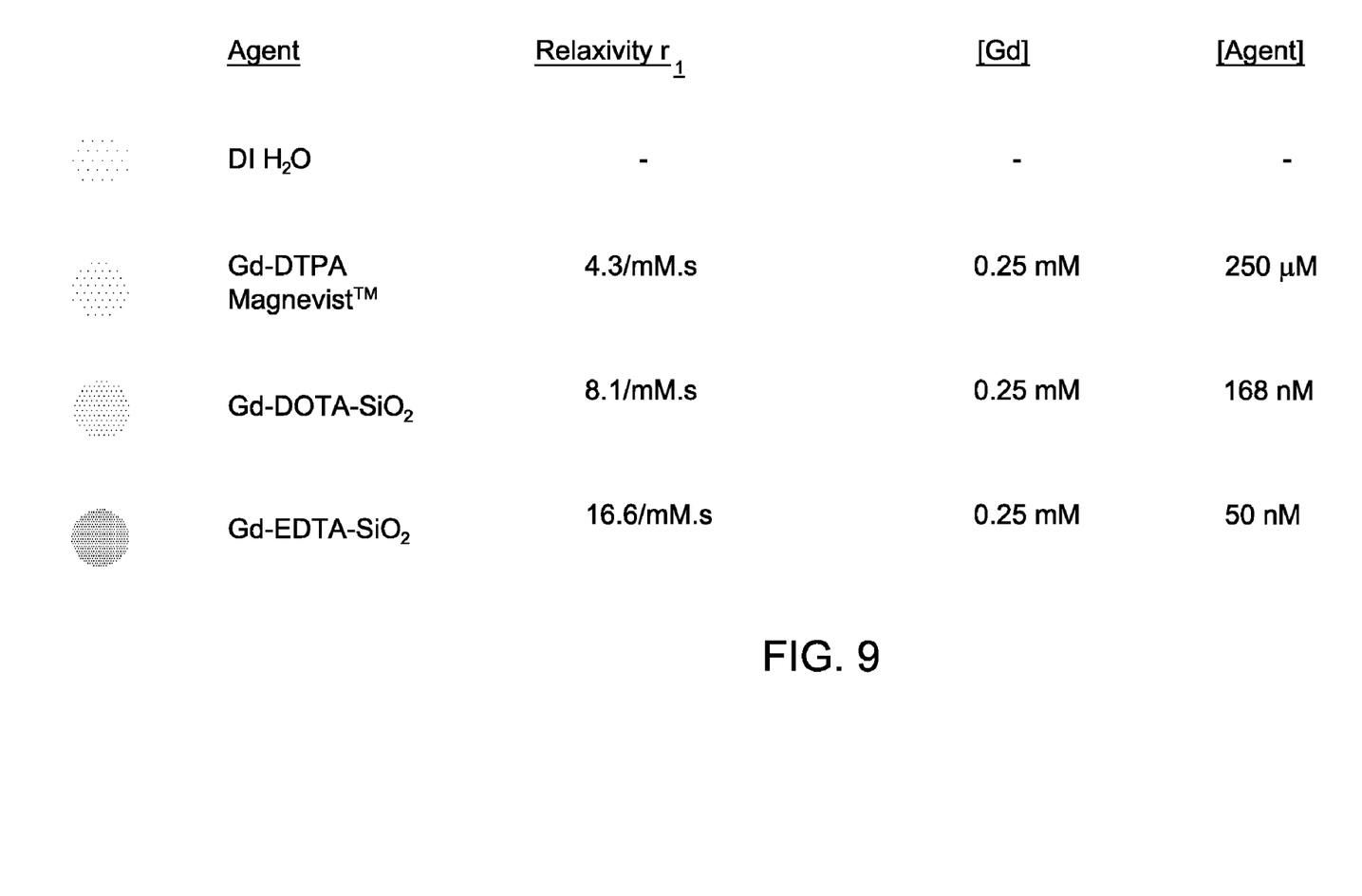
FIG. 9 shows the comparative magnetic signal intensity of commercially available contrast agent Magnevist™, Gd-EDTA, Gd-DOTA functionalized silica nanoparticles, and deionized water.

Phantom studies of the silica-based nanoparticle MR agents were carried out on a GE 1.5T MR scanner using standard FSPGR pulse T1 weighted MR pulse sequences (Te=3 ms, Tr=150 ms, slice thickness=2 mm). The silica-based nanoparticle MR agents, SiO$_2$GdDOTA and SiO2GdEDTA, were prepared in buffer (pH 7, 10 mM $Et_3NHOAc$ buffer, 150 mM saline) and their MR signal compared to that of GdDTPA (0.25 mM [Gd], pH 7, 10 mM $Et_3NHOAc$ buffer, 150 mM saline) and buffer. The silica-based MR agents showed T1 brightening signal under T1-weighted conditions, as summarized in Table 2, and displayed significant improvement in signal enhancement in comparison to the clinical molecular MR agent, GdDTPA. Table 2 shows MR properties of Gd—SiO$_2$

TABLE 2

| Agent | % Enhancement DI | % Enhancement GdDTPA |
|---|---|---|
| DI | 0 | — |
| Gd DTPA | 148 | 0 |
| SiO$_2$GdDOTA | 255 | 43 |
| SiO$_2$GdEDTA | 325 | 72 |

The percent enhancement of signal of chelator-functionalized nanoparticles over deionized water (DI) and small GdDTPA molecules were measured on a GE 1.5T MR scanner using standard FSPGR pulse T1 weighted MR pulse sequences (Te=3 ms, Tr=150 ms, slice thickness=2 mm). The values are shown in Table 2. There is an appreciable increase of percent enhancement of signal of chelator-functionalized nanoparticles over deionized water (DI) and small GdDTPA molecules.

Another aspect of the invention is to provide a method of making of water-soluble nanoparticles. The method comprises the steps of: providing an MR-passive core having a coating comprising functionalized organosilane moieties having amine functionalized group and reacting with a chelator.

In one embodiment the organosilane reagent is (3-aminopropyl)trimethoxysilane (APTMS). In one embodiment the chelator is activated before reacting with the coating. The activation was carried out using known methods such as formation of anhydrides, acid chlorides, esters etc. In one preferred embodiment, the activation of the functional group of the chelator is carried out by forming an active ester.

In a later step the chelator-functionalized nanoparticle was solubilized in a polar protic solvent to produce water-soluble nanoparticle containing chelator compound.

In one embodiment the chelator is a macrocyclic compound. In other embodiment the chelator is linear compound.

In another embodiment the method further includes a purification step. In one embodiment the chelator-functionalized nanoparticle was purified using High molecular weight (MW) based purification method. High molecular weight based purification is a method that utilizes the molecular weight of the particle for separation. The non-limiting examples include size exclusion chromatography, dialysis, or ultrafiltration. In a subsequent step the chelator-functionalized nanoparticle was further reacted with excess salt of the corresponding paramagnetic metal to form paramagnetic metal complexed nanopaticle. In an embodiment the paramagnetic metal complexed nanoparticles are purified by dialysis.

The advantage of this method compared to the common low molecular weight techniques is the ease of purification. In the case where the chelate complex is attached to the organosilane moiety prior to the nanoparticle core, the low molecular weight separation techniques, such as chromatography, necessary to purify the precursors are more involved. The high molecular weight technique is generally combined with others that further separate molecules by other characteristics, such as acidity, basicity, charge, and affinity for certain compounds.

In another embodiment, the chelator-functionalized nanopaticle was further functionalized with a pharmacokinetic enhancer.

Methods of Using Silica-based Nanoparticles

In one aspect, the present invention also provides methods of imaging. In one embodiment the nanoparticles are used as T1 agent. In another embodiment the present invention provides methods for efficiently introducing the nanoparticle into diseased cells. In some embodiments, the nanoparticle is introduced into the cells ex vivo. In other embodiments, the nanoparticles are directly introduced into the subject's body.

An aspect of the invention also encompasses a method for obtaining an MR image of a tissue or an organ of an animal or a human subject comprising:
(a) administering to the subject, an effective amount of a magnetic resonance imaging contrast agent in a physiologically acceptable medium, wherein the magnetic resonance imaging contrast agent comprises the chelator-functionalized nanoparticle and (b) recording the MR image of the tissue or organ of the subject.

An aspect of the invention also encompasses a method of diagnosis comprising administering to a mammal a contrast effective amount of the chelator-functionalized nanoparticles suspended or dispersed in a physiologically tolerable carrier and generating a magnetic resonance image of said mammal.

EXAMPLES

Practice of the invention will be still more fully understood from the following examples, which are presented herein for illustration only and should not be construed as limiting the invention in any way.

Unless otherwise noted, all reagent-grade chemicals were used as received, and Millipore water was used in the preparation of all aqueous solutions. Colloidal silica suspension in isopropanol (30% by wt, 15-20 nm, IPAST) was purchased from Nissan Chemical Industries (Tokyo, Japan). Glacial acetic acid was purchased from Fisher Scientific. Tetraethyl orthosilicate (TEOS), aqueous ammonia solution (NH$_4$OH, 71 wt % water, 29 wt % ammonia), 3-(aminopropyl)trimethoxysilane (APTMS), succinic anhydride, and N-(3-Dimethylaminopropyl)-N'-ethylcarbodiimide hydrochloride (EDC, SigmaUltra) were purchased from Aldrich Chemical (Milwaukee, Wis.). Organosilanes 3-(trihydroxysilyl)-propylmethylphosphonate (THPMP), 3-(aminopropyl)triethoxysilane (APTES), N-(triethoxysilylpropyl)-o-polyethylene oxide urethane, 2-[methoxy(polyethyleneoxy)propyl]trimethoxysilane, and N-(trimethoxysilylpropyl) ethylenediamine, triacetic acid, sodium salt (EDTA-TMS, 45% in water) was purchased from Gelest (Tullytown, Pa.). Cyclic ligands 1,4,7,10-Tetraazacyclododecane-1,4,7,10-tetraacetic acid (DOTA) was purchased from Macrocyclics (Dallas, Tex.). Sulfo-NHS (N-hydroxysulfosuccinimide) was purchased from Pierce Biotechnology (Rockford, Ill.).

Example 1

EDTA-SiO2: Surface Modification of Silica Nanoparticles with EDTA-TMS

Figure 4:
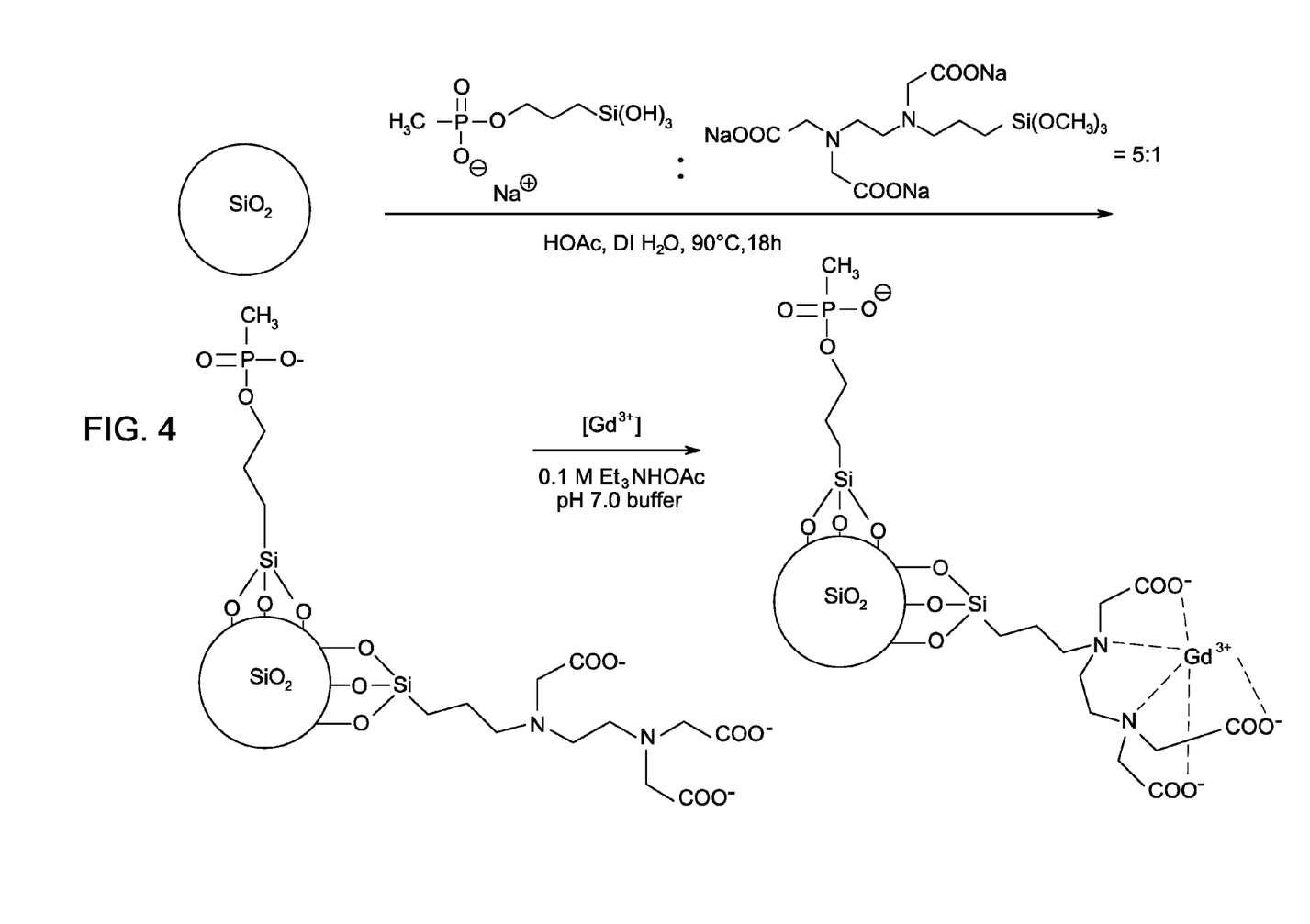
FIG. 4 depicts the hybrid coating on silica nanoparticles using EDTA-TMS, and THPMP.
Figure 5:
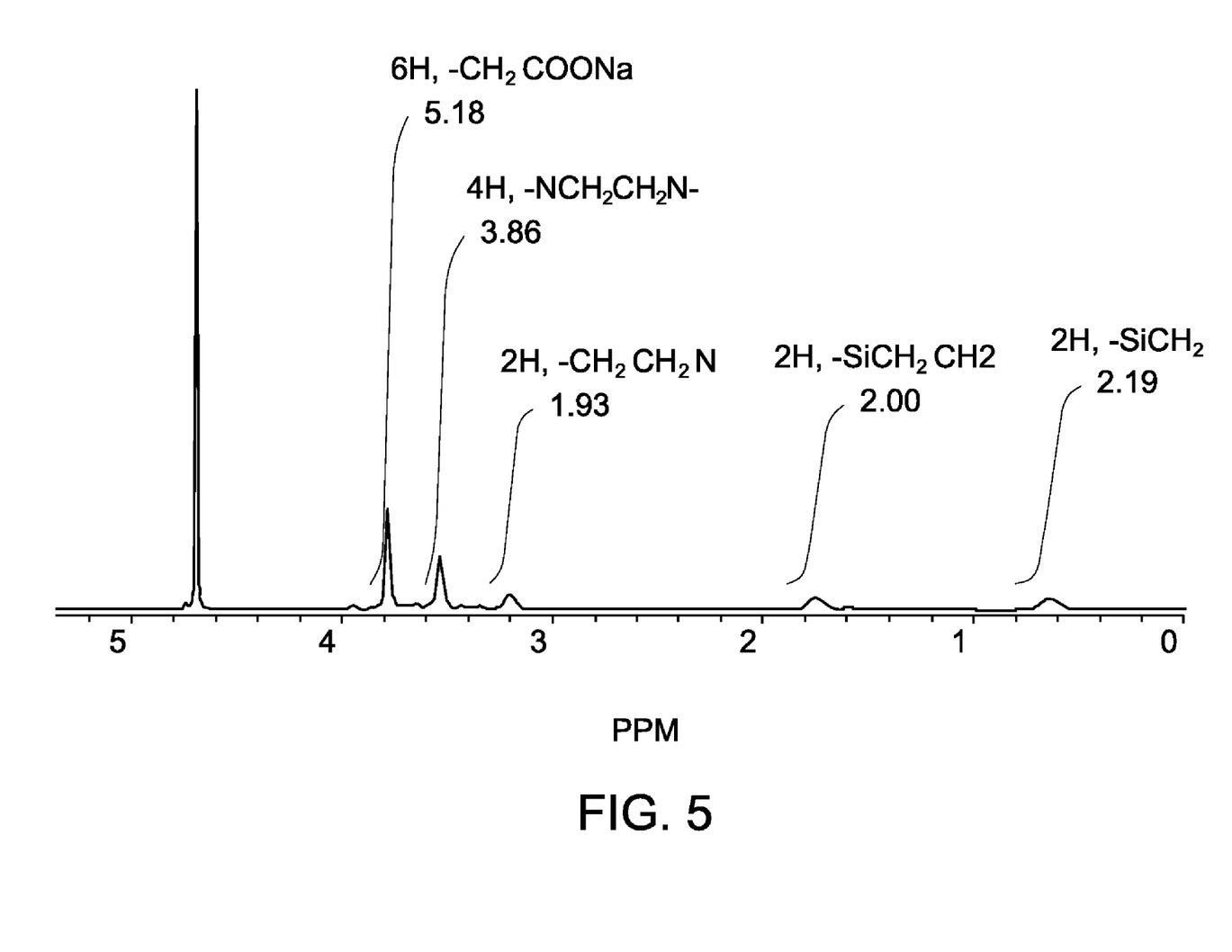
FIG. 5 shows $^1$H NMR chelator-functionalized silica nanoparticles.
Figure 6:
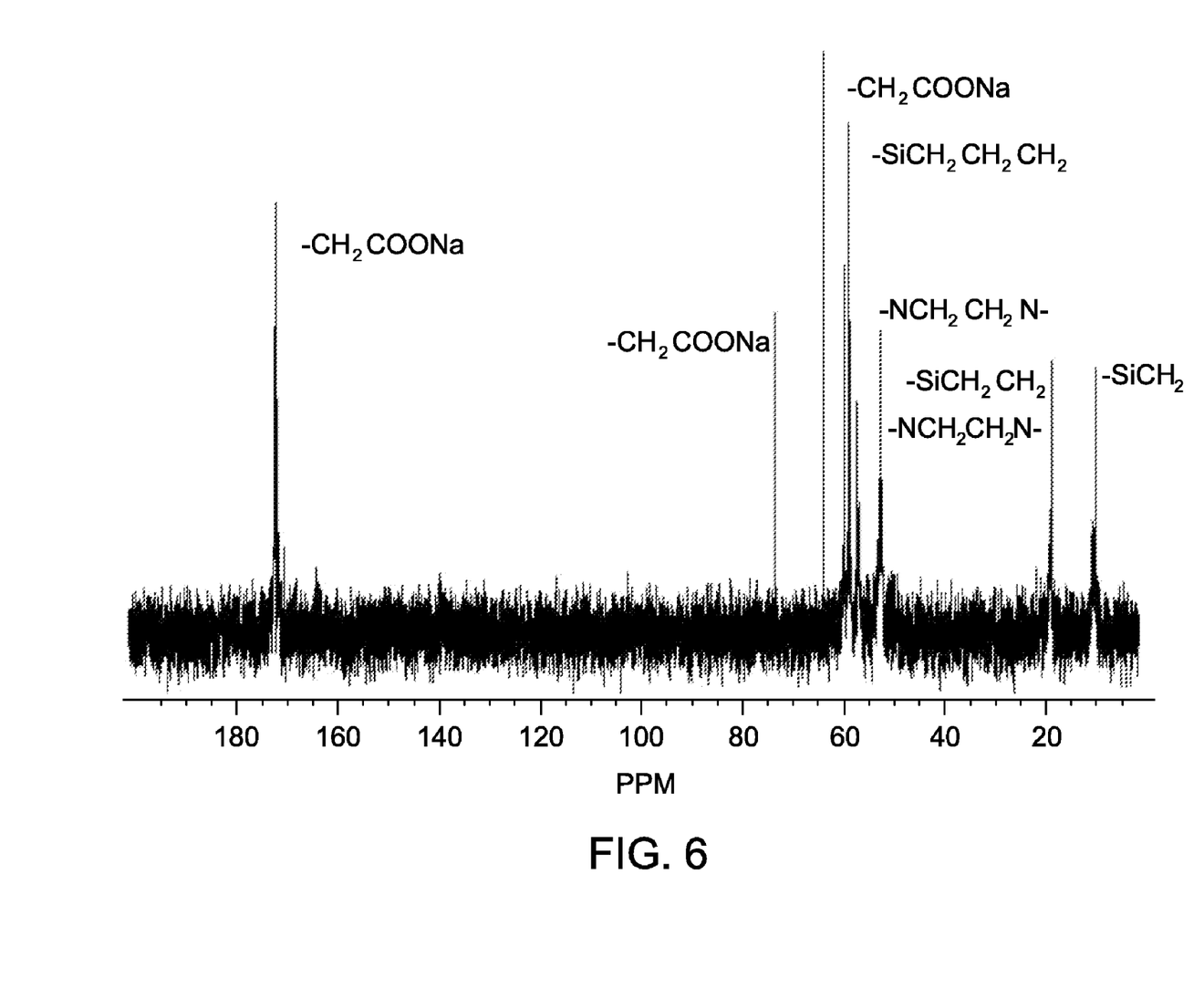
FIG. 6 shows $^{13}$C NMR of chelator-functionalized silica nanoparticles.
Figure 7:
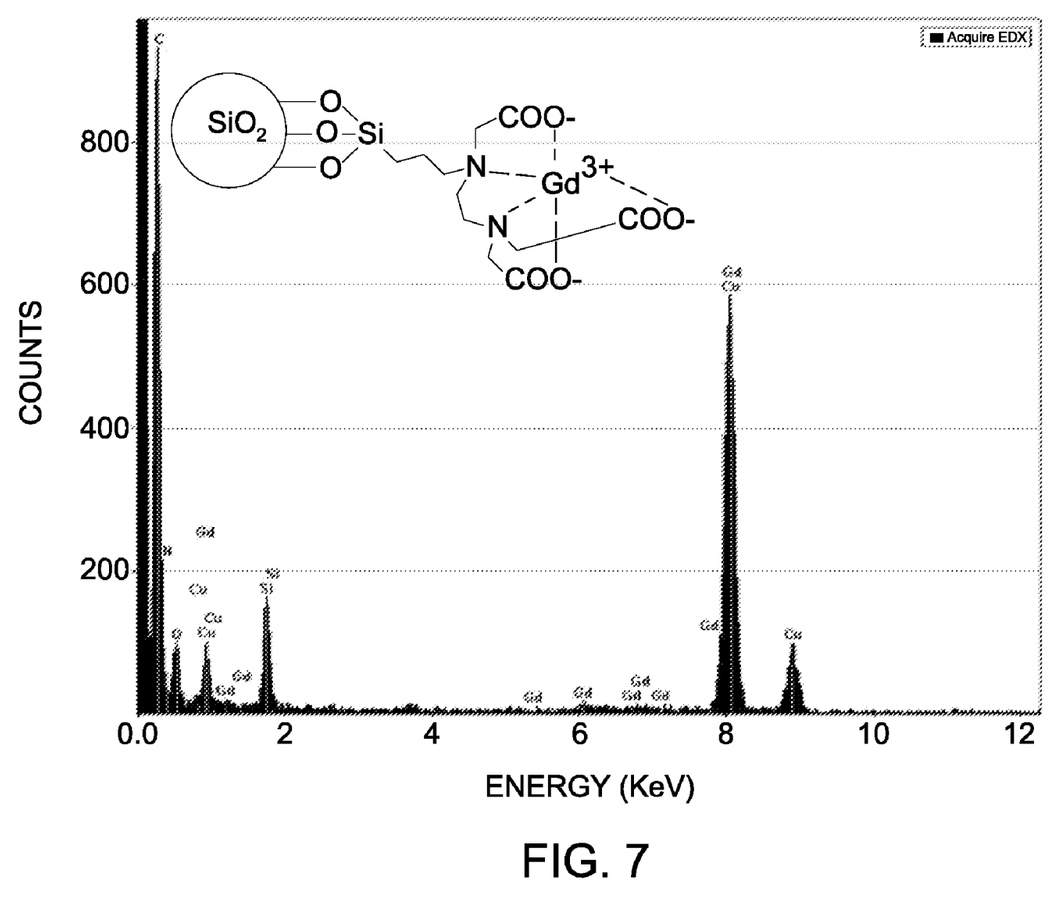
FIG. 7 shows TEM micrographs of EDTA functionalized silica nanoparticles
Figure 8:
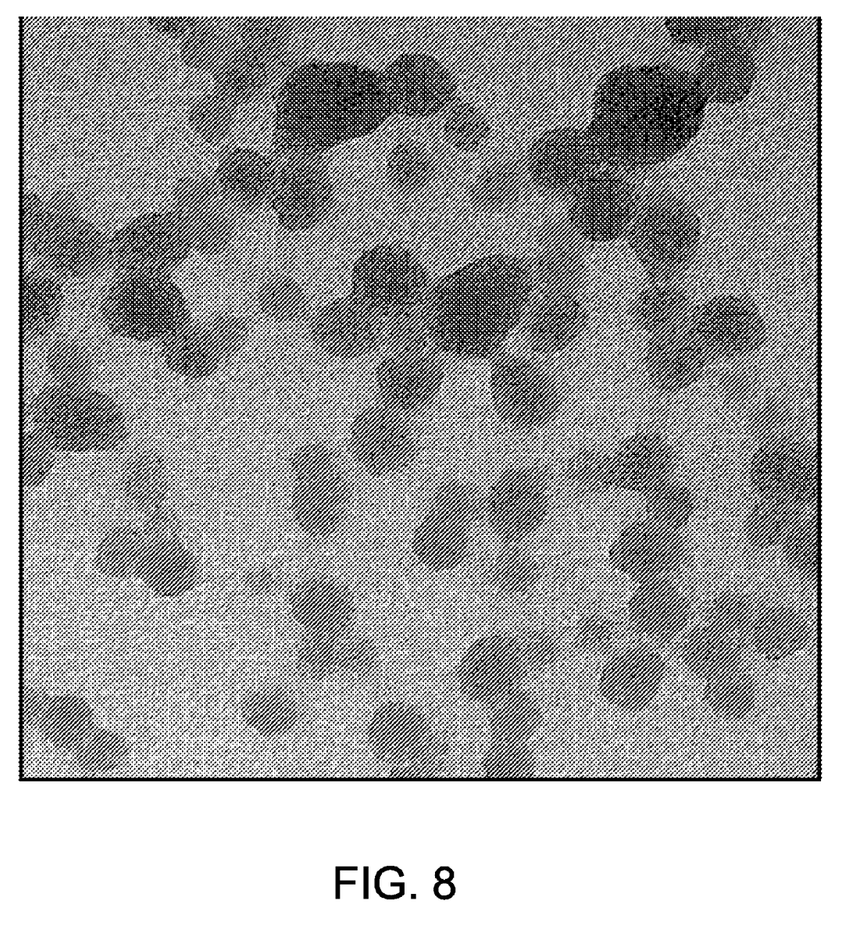
FIG. 8 shows the TEM micrographs of particle size distribution of the nanoparticles

EDTA functionalized silica nanoparticles were synthesized by modification of commercially available silica nanoparticles (IPAST, Nissan Chemical Industries, Tokyo, Japan) using N-(trimethoxysilylpropyl)ethylenediamine, triacetic acid, sodium salt (EDTA-TMS, 45% in water, Gelest, Morrisville, Pa.) as follows: To a 200 mL round bottom flask equipped with a Teflon-coated stir bar was added 50 mL deionized H$_2$O and 20.16 mL EDT-TMS (24.7 mmol). To this homogeneous solution was added 7.5 mL concentrated acetic acid (HOAc) and 5 mL IPA-ST (24.7 mmol SiO$_2$). The reaction mixture was heated 90° C. for 18 h. After 30 s, reaction mixture turned to be homogeneous. After 18 h, solution was cooled to room temperature and was basified with 5% NaOH aqueous solution to neutral (pH ~7). The solution was dialyzed three times over 24 h against deionized H$_2$O. The particle suspension was filtered through a 0.2 mm syringe filter and was stored at room temperature on shelf. No sign of aggregation was observed using DLS after a month.

Example 2

THPMP-SiO$_2$: Surface Modification of Silica Nanoparticles with THPMP

THPMP functionalized silica nanoparticles were synthesized by modification of commercially available silica nanoparticles (IPAST, Nissan Chemical Industries, Tokyo, Japan) using 3-(trihydroxysilyl)-propylmethylphosphonate (THPMP, 42% in water, Gelest, Morrisville, Pa.) as follows: To a 250 mL round bottom flask equipped with a Teflon-coated stir bar was added 100 mL deionized H$_2$O and 11.21 mL THPMP (24.7 mmol). To this homogeneous solution was added 15 mL concentrated acetic acid (HOAc) and 10 mL IPA-ST (49.43 mmol SiO$_2$). The reaction mixture was heated less than 90° C. for 18 h. After 30 s, reaction mixture turned to be homogeneous. After 18 h, solution was cooled to room temperature and was basified with 5% NaOH aqueous solution to neutral (pH ~7). The solution was dialyzed three times over 24 h against deionized H$_2$O. The particle suspension was filtered through a 0.2 mm syringe filter and was stored at room temperature on shelf. No sign of aggregation (based on DLS) was observed after at least one month.

Example 3

EDTA-THPMP-SiO$_2$: Surface Modification of Silica Nanoparticles with EDTA-TMS and THPMP EDTA-THPMP functionalized hybrid silica nanoparticles were synthesized by modification of commercially available silica nanoparticles (IPAST, Nissan Chemical Industries, Tokyo, Japan) using N-(trimethoxysilylpropyl) ethylenediamine, triacetic acid, sodium salt (EDTA-TMS, 45% in water, Gelest, Morrisville, Pa.) and 3-(trihydroxysilyl)-propylmethylphosphonate (THPMP, 42% in water, Gelest, Morrisville, Pa.) as follows: To a 250 mL round bottom flask equipped with a Teflon-coated stir bar was added 100 mL deionized $H_2O$ and 4.49 mL THPMP (9.89 mmol) and 1.6 mL EDTA-TMS (1.95 mmol). To this homogeneous solution was added 15 mL concentrated acetic acid (HOAc) and 10 mL IPA-ST (24.7 mmol $SiO_2$). The reaction mixture was heated less than 90° C. for 18 h. After 30 s, reaction mixture turned to be homogeneous. After 18 h, solution was cooled to room temperature and was basified with 5% NaOH aqueous solution to neutral (pH ~7). The solution was dialyzed three times over 24 h against deionized $H_2O$. The particle suspension was filtered through a 0.2 mm syringe filter and was stored at room temperature on shelf. No sign of aggregation (based on DLS) was observed after at least one month.

Example 4

Incorporation of Gadolinium Ions onto EDTA-SiO$_2$ Nanoparticle Surface

Figure 1:
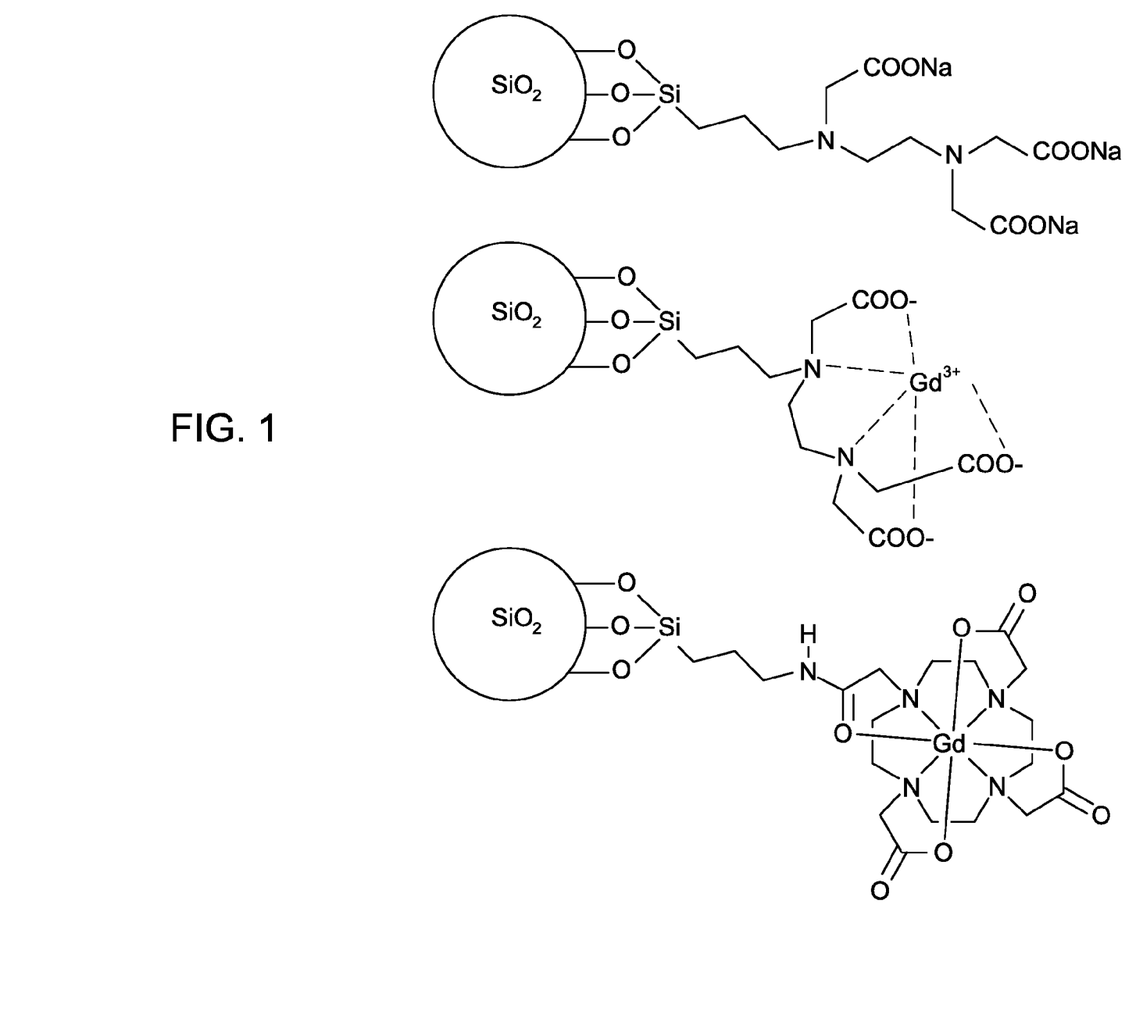
FIG. 1 depicts representative chelator-functionalized nanoparticles that are useful for MR imaging.
Figure 2:
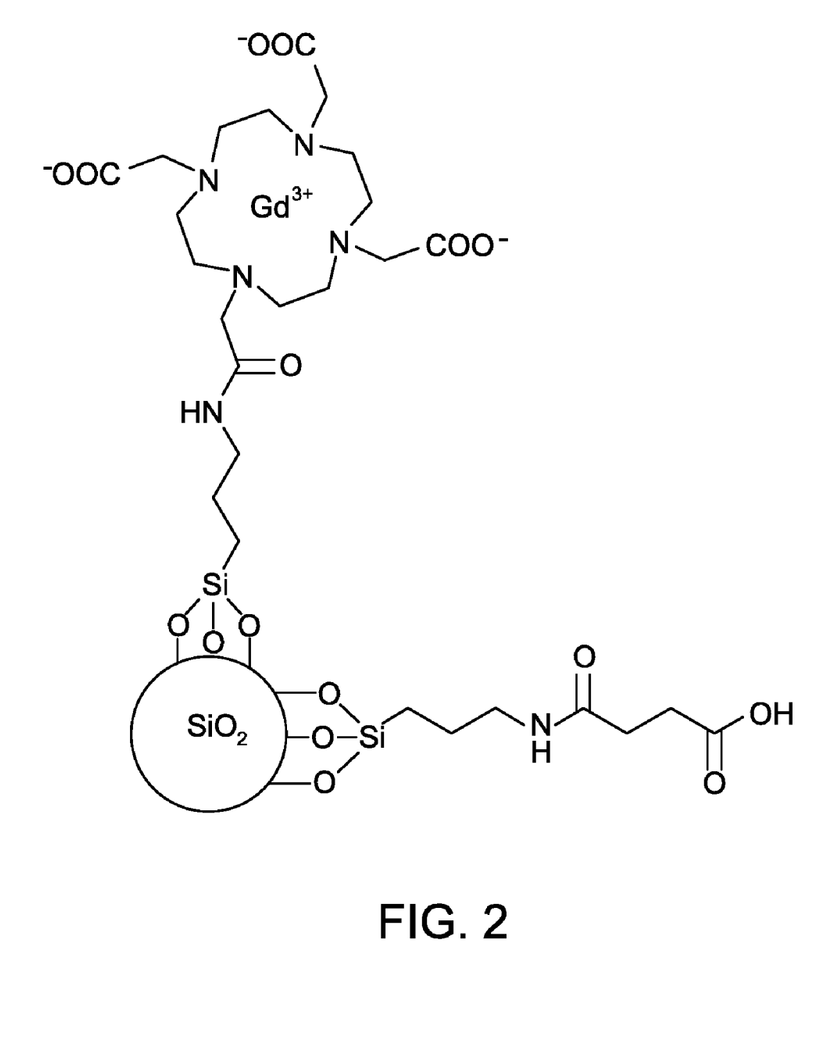
FIG. 2 shows an example of DOTA functionalized nanoparticles, where the organosilane coating of the nanopaticle is further functionalized with a pharmacokinetic modifier.
Figure 3:
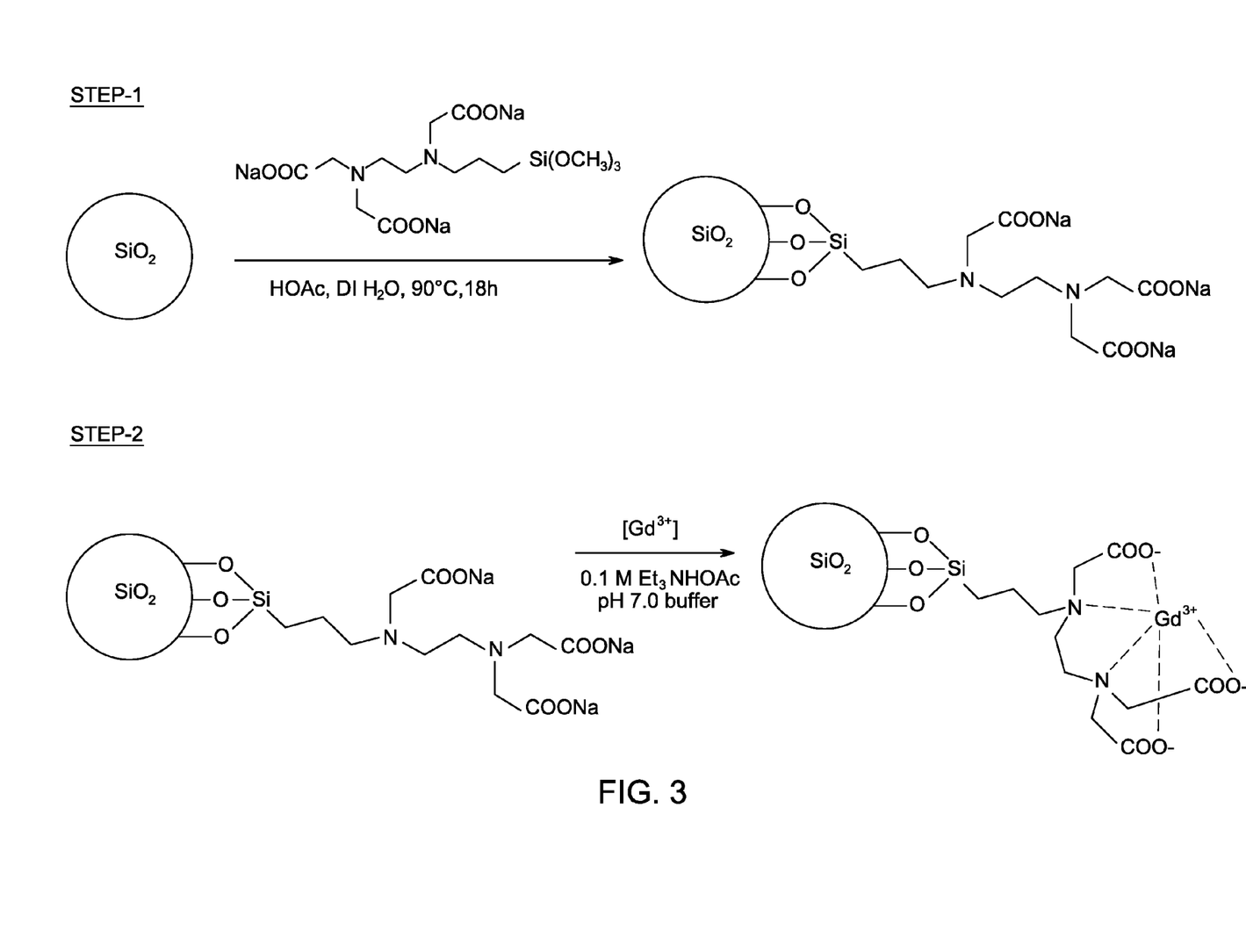
FIG. 3 depicts the synthesis method for generating the chelator-functionalized silica nanoparticles and incorporation of Gd (III) ion into the chelator.

Thousands of Gadolinium ions may be incorporated onto silica nanoparticles surface via coordination with EDTA chelators presented on EDTA-SiO$_2$ particle surface. Gadolinium Citrate solution was prepared in 10 mM Et$_3$NHOAc (pH 7.0 with 0.15M NaCl) as mentioned: 0.6 M GdCl3 aqueous solution and 0.6 M sodium citrate solution were mixed in 1:1 volume ratio. Brief vortex of the mixture afforded 0.3 M Gadolinium Citrate solution. To a 20 mL scintillation vial equipped with a Teflon-coated stir bar was added 5 mL 10 mM Et$_3$NHOAc (pH 7.0 with 0.15M NaCl) buffer and 1.67 mL of 0.3 M Gadolinium Citrate solution. Then 5 mL of EDTA-SiO$_2$ (0.6% EDTA-SiO$_2$ in deionized H$_2$O by wt %) was added to the reaction mixture. The solution was stirred under room temperature for 18 hours. Reaction mixture stayed clear. The Gd solution was purified by dialyzing against DI H$_2$O overnight in a SnakeSkin (10,000 MWCO) dialysis tube. Dialyzed solution was recovered and stored at room temperature on shelf. No sign of aggregation was observed (based on DLS) after at least one month.

Example 5

APTMS-SiO$_2$: Surface Modification of Silica Nanoparticles with APTMS

To a 200 mL RB flask equipped with a Teflon-coated stir bar was added 30 mL DI H$_2$O, 18 mL HOAc, 5.4 mL of APTMS (29.7 mmol), and 30 mL IPA-ST (1458.4 mmol) successively. Reflux the reaction mixture under 80° C. overnight. After 18 h, reaction mixture was cooled to room temperature and 25 mL of ethylene glycol was added. Remove solvent by evaporating under vacuum for 2 h at 50° C. and residue solution was dialyzed against 24 L DI H$_2$O in a SnakeSkin dialysis tube (MWCO 10K). Water is changed every 4 h.

Example 6

Attachment of DOTA onto Silica Nanoparticle Surface via EDC Coupling

To a 50 mL RB flask equipped with a stir bar was added 1.64 g DOTA (4.053 mmol) and 10 mL 0.5 M pH 7.0 Et$_3$NHOAc buffer. After brief sonication, all solids were dissolved. Then 847.5 mg EDC (4.421 mmol), 800 mg Sulfo-NHS (3.684 mmol) were added to the solution. Solution was homogeneous and pH was ~5.5. The reaction mixture was stirred at room temperature for 2 h. After 2 h, 25 mL APTMS—SiO$_2$ (46 mg/mL, 19.14 mmol) aqueous solution was added to the reaction mixture. Solution became cloudy immediately. pH of the solution was adjusted by adding 0.8 mL Et$_3$N and the pH of the solution became ~8. The reaction mixture was stirred overnight (~18 hours). After 18 hours, to the reaction mixture was added 369 mg of succinic anhydride (3.684 mmol). The pH of the solution was adjusted using Et$_3$N to pH ~9 and left it stirring for another 4 h. Resulting solution was dialyzed against 24 L DI H$_2$O in a SnakeSkin dialysis tube (MWCO 10K). Water was changed every 4 hours.

Example 7

Incorporation of Gadolinium Ions onto DOTA-SiO$_2$ Nanoparticle Surface

Thousands of Gadolinium ions were incorporated onto silica nanoparticles surface via coordination with DOTA ligands presented on DOTA-SiO$_2$ particle surface. Gd Citrate solution was prepared by mixing 0.6 M GdCl$_3$ solution and 0.6 M Na$_3$Citrate with volume ratio of 1:2 in a 15 mL conical tube. To a 20 mL vial equipped with Teflon coated stir bar was added 5 mL of 0.1 M Et$_3$NHOAc buffer and 5 mL DOTA-SiO$_2$ (23 mg/mL, 1.91 mmol) solution. Solution became cloudy. To this solution was added 9.571 mL Gd Citrate (0.2 M, 1.91 mmol) solution. The pH of the solution was adjusted to ~9 with Et$_3$N. The solutions were stirred at RT overnight (~16 h). The Gd solution was purified by dialyzing against 24 L DI H$_2$O in a SnakeSkin dialysis tube (MWCO 10K). Water was changed every 4 h. Some physical characteristics of the resulting agents were listed above in Table 2.

Table 3 shows the effect of EDTATMS equivalents on 25 nm SiO$_2$ nanoparticle labeling.

TABLE 3

| EDTA-TMS Equiv | Gd/Si (ICP) | No. Chelators/nanoparticle$^{-1}$ | No. Chelators/nm$^{-2}$ |
|---|---|---|---|
| 1 | 0.1498 | 11330 | 6.3 |
| 0.5 | 0.1051 | 7552 | 4.2 |
| 0.2 | 0.1148 | 8345 | 4.6 |
| 0.1 | 0.0776 | 5409 | 3.0 |
| 0.02 | 0.0272 | 1802 | 1.0 |
| 0.005 | 0.0062 | 403 | 0.2 |

Varying gadolinium ions loading on SiO$_2$ nanoparticle surface. Gadolinium ion loading on silica nanoparticles surface may be controlled by varying different amount of chelators presented on SiO$_2$ particle surface. Various EDTA-SiO$_2$, THPMP—SiO$_2$, and EDTA-THPMP-SiO$_2$ nanoparticles with different amount of EDTA chelators on their surfaces have been prepared according to procedures described above. The resulting gadolinium loaded nanoparticles were purified by dialyzing against DI H$_2$O overnight in a SnakeSkin (10,000 MWCO) dialysis tube. Dialyzed solution was further washed by centrifiltration (10,000 MWCO at 3500 rpm for 5 min) six times and retained solution was stored at room temperature on shelf. Gadolinium and silicon concentration were measured by ICP elemental analysis and were used to calculate Gd loading on SiO$_2$ nanoparticle surface. As shown in Table 3, the loading of Gd on the SiO$_2$ nanoparticle was controlled via the reaction stoichiometry of the SiO$_2$ nanoparticle with the organosilane, EDTA-TMS, and thereby chelator incorporated onto the nanoparticle surface. A low EDTA-TMS:SiO$_2$ reactant ratio of 0.005 provided a moderately surface functionalized nanoparticle (400 chelators per particle), whereas increasing the EDTA-TMS:SiO$_2$ reactant ratio resulted in the formation of SiO$_2$ nanoparticles with progressively higher surface functionalization, in general. A 1:1 stoichiometry of EDTA-TMS:SiO$_2$ nanoparticle afforded a surface functionalized nanoparticle with approximately 11000 chelators attached, which could then be used to bind Gd. Nanoparticles of approximately 25 nm were obtained using the experimental conditions described above and thus the loading of the chelated metal per unit area of the nanoparticle could be varied from 0.2 to 6.3 chelators.nm$^{-2}$.

Equivalents

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:

1. A nanoparticle comprising:
    an MR-passive core having a coating comprising functionalized organosilane moieties and a plurality of linear chelators, wherein each of the plurality of linear chelators is attached to the passive core via an organosilane moiety through a single point of attachment; and
    a plurality of non-paramagnetic counterions, wherein each of the plurality of non-paramagnetic counterions is complexed with the linear chelator; and wherein the D$_H$ of the nanoparticle is less than 35 nm.

2. The nanoparticle of claim 1, wherein the linear chelator selected from ethylenediamine tetraacetic acid (EDTA), diethylenetriaminepentaacetic acid (DTPA), or Triethylenetetraminehexacetic acid (TTHA), N-tris(2-aminoethyl)amine-N',N',N'',N'',N''',N'''-hexaacetate (TTAHA) or combinations thereof.

3. The nanoparticle of claim 1, wherein the passive core comprises an inorganic material selected from silicon, aluminum, titanium, germanium, or derivatives thereof.

4. The nanoparticle of claim 3, wherein the passive core comprises silica.

5. The nanoparticle of claim 1, wherein the non-paramagnetic counterions are selected from sodium, triethylammonium, potassium, calcium, dimegulamine, protons, or combinations thereof.

6. The nanoparticle of claim 1, wherein the non-paramagnetic counterions are substituted with paramagnetic ions selected from Gd, Fe, Mn, or combinations thereof.

7. The nanoparticle of claim 6, wherein the surface density of paramagnetic ions complexed with the linear chelator is between 0.2 to 6 complexed paramagnetic ions per square nanometer.

8. The nanoparticle of claim 6, wherein an r2/r1 ratio of the nanoparticle is greater than 1 and less than 2.5.

9. The nanoparticle of claim 1, wherein the organosilane moiety is selected from N-(trimethoxysilylpropyl)ethylene diamine triacetic acid trisodium salt, N-(trimethoxysilylpropyl)-O-polyethylene oxide urethane, N-(trimethoxysilyl) propyl succinic anhydride, N-(trihydroxysilyl)propylmethylphosphonate, sodium salt, 2-(4-chlorosulfonylphenyl) ethyltrimethoxysilane, 3-aminopropyltriethoxysilane, or combinations thereof.

10. The nanoparticle of claim 1, wherein the nanoparticle further comprises a pharmacokinetic modifier selected from PEG, dextran, alkyl chain, ethylene glycol, poly L,L-lactic acid (PLLA), poly-caprolactone (PCL), 3-(trihydroxysilyl)-propylmethylphosphonate (THPMP), poly(2-methyl-2-oxazolidinone), poly(2-ethyl-2-oxazolidinone), poly(vinylpyrrolidinone), poly(arylamides), phosphonates, or combinations thereof.

* * * * *